(12) United States Patent
Barker et al.

(10) Patent No.: US 8,287,559 B2
(45) Date of Patent: Oct. 16, 2012

(54) SURGICAL CLIPS WITHOUT PROTRUSIONS

(75) Inventors: Stephen George Edward Barker, London (GB); Simon John Hollingsworth, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 10/543,720

(22) PCT Filed: Jan. 21, 2004

(86) PCT No.: PCT/GB2004/000171
§ 371 (c)(1),
(2), (4) Date: Sep. 26, 2005

(87) PCT Pub. No.: WO2004/066849
PCT Pub. Date: Aug. 12, 2004

(65) Prior Publication Data
US 2006/0200179 A1    Sep. 7, 2006

(30) Foreign Application Priority Data
Jan. 29, 2003   (GB) .................................. 0302098.9

(51) Int. Cl.
*A61B 17/08* (2006.01)
(52) U.S. Cl. ....................................................... 606/158
(58) Field of Classification Search .................. 606/157, 606/158, 151; 623/2.38; 128/831, 843
See application file for complete search history.

(56) References Cited

U.S. PATENT DOCUMENTS

| | | | |
|---|---|---|---|
| 3,766,925 A | 10/1973 | Rubricius | |
| 3,926,195 A | 12/1975 | Bleier et al. | |
| 4,016,883 A * | 4/1977 | Wright, Jr. | 606/158 |
| 4,112,944 A | 9/1978 | Williams | |
| 4,390,019 A | 6/1983 | LeVeen et al. | |
| 4,449,531 A | 5/1984 | Zwaskis et al. | |
| 4,667,671 A * | 5/1987 | Danzig | 606/143 |
| 5,575,802 A * | 11/1996 | McQuilkin et al. | 606/151 |
| 5,624,454 A | 4/1997 | Palti et al. | |
| 5,645,553 A * | 7/1997 | Kolesa et al. | 606/157 |

(Continued)

FOREIGN PATENT DOCUMENTS

AU    2001294651    4/2002

(Continued)

OTHER PUBLICATIONS

International Search Report of PCT/GB2004/000171, mailed Jun. 28, 2004.

(Continued)

*Primary Examiner* — Gary Jackson
*Assistant Examiner* — Lindsey Bachman
(74) *Attorney, Agent, or Firm* — Vedder Price P.C.; Thomas J. Kowalski; Deborah L. Lu (57) ABSTRACT

A surgical clip (5) is provided for clipping a tubular structure (9) in vivo to ligate the tubular structure. The clip comprises first and second clip portions (6, 7). A hinge portion (8) is provided connecting the clip portions together and to enable the clip portions to be hinged together from an open clip condition to a closed clip condition thereby to ligate a tubular structure placed between the clip portions. A lock is provided for locking the clip portions together in the closed clip condition. In the closed clip condition the clip has a substantially smooth external profile, for example including blunt ends (21), so as to reduce the possibility of the clip (in use) eroding surrounding tissue structures.

58 Claims, 10 Drawing Sheets

U.S. PATENT DOCUMENTS

| | | | |
|---|---|---|---|
| 5,676,676 A * | 10/1997 | Porter | 606/158 |
| 5,697,942 A * | 12/1997 | Palti | 606/151 |
| 5,713,912 A * | 2/1998 | Porter | 606/158 |
| 5,810,853 A * | 9/1998 | Yoon | 606/151 |
| 5,817,103 A * | 10/1998 | Bell | 606/120 |
| 5,908,430 A | 6/1999 | Appleby | |

FOREIGN PATENT DOCUMENTS

| | | |
|---|---|---|
| DE | 198 58 580 C | 9/2000 |
| GB | 1 020 035 A | 2/1966 |
| GB | 1020035 A | 2/1966 |
| GB | 1420459 | 1/1976 |
| GB | 2055953 A | 2/1980 |
| GB | 2 055 953 A | 3/1981 |
| GB | 2108135 A | 7/1982 |
| GB | 2 108 135 A | 5/1983 |
| GB | 2128478 A | 9/1983 |
| GB | 2 128 478 A | 5/1984 |
| GB | 2285582 A | 12/1994 |
| GB | 2 285 582 A | 7/1995 |
| JP | 50-108786 A | 11/1977 |
| WO | 2004/080275 | 9/2004 |

OTHER PUBLICATIONS

GB Search Report of GB 0302098.9, mailed Aug. 27, 2003.
GB Search Report of GB 0302098.9, mailed Jul. 17, 2003.

* cited by examiner

SURGICAL CLIPS WITHOUT PROTRUSIONS

This application is the US national phase of international application PCT/GB2004/000171, filed 21 Jan. 2004, which designated the U.S. and claims priority of GB 0302098.9, filed 29 Jan. 2003, the entire contents of each of which are hereby incorporated by reference.

This invention relates to surgical clips for use in the occlusion or ligation of tubular structures.

Figure 1:
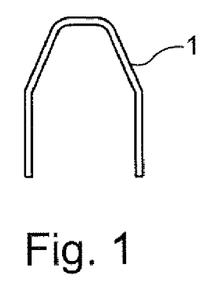
FIG. 1 is an enlarged end elevation of a prior art metal clip prior to use.
Figure 2A:
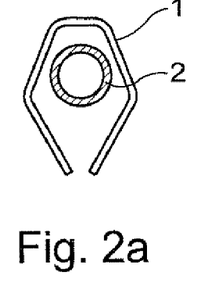
FIGS. 2a-2c show, in sequence, the clip of FIG. 1 being progressively deformed around a tubular structure so as to ligate that structure.
Figure 2B:
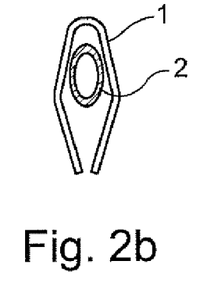
Figure 2C:
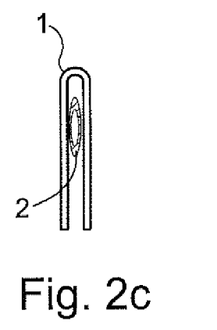

The ligation or occlusion of tubular structures such as vessels, for example arteries, veins or lymphatics, is routinely performed by clipping. Such clips may, for example, be folded metal pieces, often stainless steel or titanium, which are available in various different sizes—one such prior art clip is shown in FIG. 1. These clips are applied singly from an independent cartridge, or singly from a semi-automatic, pre-filled magazine. In either case, the clip (mounted in an applicator device) is passed across the vessel to be clipped. The applicator device is then operated. As shown in the sequence of FIGS. 2a, 2b and 2c, operation of the applicator device causes the distal (open) tips of the bent metal clip 1 to be brought together first. After the tips have been brought together so as to trap the vessel 2 within the confines of the clip, the central portions of the clip are brought together to ligate the vessel. In this way it is hoped that the vessel will not slip out of the clip during application of the clip.

There are, however, several problems associated with these prior art, metal clips.

A first problem is that vessels, such as arteries, are tubular structures (generally of circular cross-section) that have their thickness composed mainly of smooth muscle. This gives the vessels a variable degree of "substance", which might be enhanced further by a disease process affecting them, such as atheroma, calcification (especially in diabetes) or stiffening (as with hypertension). By placing a bent, flat profile metal clip across a tubular structure that does not wish to be flat, there is a risk that the vessel will slip out of the clip. This risk generally increases with vessel size.

Figure 3:
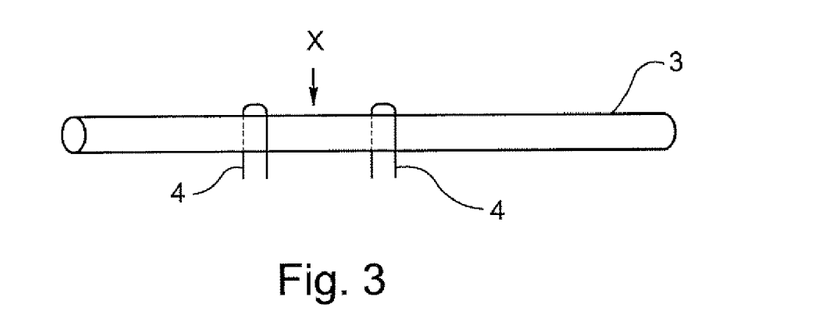
FIG. 3 is a schematic, perspective view of a vessel to be clipped and divided in continuity, showing the application thereto of two FIG. 1-*style* prior art clips.

By way of example, FIG. 3 shows a vessel 3 which is to be "clipped in continuity", prior to division. The vessel 3 has two clips 4 applied to it (spaced apart by say 1 cm) to occlude it. In FIG. 3, arrow X marks the site of the intended division of the vessel.

In the sort of situation illustrated in FIG. 3, the problem of the vessel 3 slipping out of the clips 4 is more annoying than dangerous. Provided the vessel 3 is still intact when one of the clips 4 slips off, there is no loss of blood and the surgeon can simply apply another clip (not shown). Indeed, it is quite common for a surgeon to apply a pair of clips to each side of the site to be cut so as to provide redundancy if one of the clips should slip off. Once the surgeon establishes that the clips 4 have not slipped off the vessel 3, that vessel can then be cut. A typical procedure of this sort would be where clips are used in the harvesting of long saphenous vein for cardiac or peripheral bypass use, or in colorectal surgery when dividing vessels within the mesentery.

The situation is far more dangerous, however, if a clip is being used to prevent bleeding from an already divided vessel, which vessel might be difficult for a surgeon to access. It might occur with a venous bleed within the pelvis during colorectal or urological surgery. Alternatively, the vessel might be a damaged vessel during a laparoscopic procedure, for example a torn intercostal vein encountered during a laparoscopic cervical sympathectomy. In such a situation, if an applied clip slips off the vessel significant volumes of blood can be lost during the time taken to apply one or more further clips.

A second problem can occur even when a prior art clip is applied successfully. The closed ends of prior art metal clips can be relatively sharp and rough. As a result these ends can erode into adjacent structures in much the same way as suture ends of prolene, at the top end of an aortic graft anastomosis, are thought to erode into the adjacent duodenum, causing an aorto-enteric fistula. As a result, vascular surgeons would hesitate to place a prior art, metal clip adjacent to the femoral vein, for example at the sapheno-femoral junction, so as to ligate, for example, the deep pudendal venous tributary, for fear of the clip ends eroding into the femoral vein, causing bleeding and the possibility also of thrombosis.

Additionally, if clips are used close to the skin surface, for example in harvesting long saphenous vein, it is possible that the clips can easily be felt by the patient through the closed skin, which is undesirable.

A third problem can arise as a result of the prior art clips being metallic. Sometimes patients post-operatively require a Computerised Tomography (CT) or Magnetic Resonance Imaging (MRI) scan. In some MRI scanners the metal of the clip can be caused to "vibrate" dramatically in the created magnetic field, causing heating of the clip and local tissue damage. In a CT scanner the presence of the metal clip can cause a "starburst" artefactual effect on the final film produced, which effect may cloud local pathology, for example a small carcinoma in the head of the pancreas.

A fourth problem can arise with prior art clips when a vessel is to be divided in continuity, as described above in conjunction with FIG. 3. In such a situation it is common for the clips to need to be placed at least several millimeters apart, maybe even up to a centimeter or more, to allow the scissors or knife access to cut, as well as to minimize the risk of the cutting implement dislodging the clips. This need to leave at least several millimeters between a clip and what will end up being the cut end of a vessel can have adverse consequences.

For example, it increases the length of vessel to which the surgeon requires access. This is exacerbated in the event that the surgeon feels it necessary to provide a plurality of clips to either side of the cutting site so as to provide an improved safety margin. In certain procedures a surgeon may only have a very short length of vessel (for example 1 cm) accessible, so the access demands associated with prior art clips can lead to practical problems.

In addition, the result of the clip spacing being such that, after vessel division, it leaves several millimeters between a clip and the cut end of a vessel can theoretically cause problems with neovascularization. This is seen, for example, in the recurrence of varicose veins in the groin following ligation and division of long saphenous vein tributaries. This arises, in theory, because the cut ends of the vessel expose endothelium. The longer the end of a vessel between the cut vessel end and the clip closest to the cut end the greater is the exposed amount of endothelium. This results in production of vascular endothelial growth factor (VEGF), which can pool in the area adjacent to the cut vessel ends. This in turn encourages the endothelium to divide, stimulating new vessel formation to try to "bridge the gap", i.e. to reconnect the opposed cut ends of the vessel. In the event that it were possible for a surgeon to be secure in the knowledge that a vessel is clipped in such a way that the clip would be totally secure, then the surgeon could have the confidence to place clips closer together prior to dividing a vessel in continuity. When the vessel is then subsequently divided between the clips the distance from each clip to the cut end of its respective vessel would be minimised, thereby exposing the minimum of endothelium, minimizing growth factor release and minimizing the risks for neovascularization.

According to the present invention there is provided a surgical clip for clipping a tubular structure in vivo so as to ligate the tubular structure, the clip comprising:

first and second clip portions; and a hinge portion connecting said clip portions together to enable said clip portions to be hinged together from an open clip condition to a closed clip condition so as to ligate a tubular structure placed between said clip portions.

According to a first aspect of the present invention the clip further comprises a lock for locking said clip portions together in said closed clip condition, in which condition the clip has a substantially smooth exterior profile so as to reduce the possibility of the clip eroding tissue structures surrounding the clip in use. In this closed clip condition the clip is substantially free of external projections.

Advantageously the lock comprises a first lock portion which protrudes from the first clip portion to terminate at a distal end, said distal end of said first lock portion being arranged to be substantially shielded from projecting into said surrounding tissue structures in said closed clip condition. Advantageously said distal end of said first lock portion is arranged to be substantially shielded from projecting into said surrounding tissue structures by intimate nesting of the first lock portion with the body of the second clip portion. For example, the second clip portion may be provided with a recess to receive said distal end of said first lock portion in said closed clip condition to shield said distal end from projecting into said surrounding tissue structures. The recess may be an open-sided channel, so that at least one side of the distal end of the first lock portion is not shielded by the second clip portion from contact with surrounding tissue structures. It is, however, preferred for the recess to be a hole, so that the distal end of the first lock portion will be surrounded in the closed clip condition so as to be internally received within the body of the second clip portion. By being internally received within the body of the second clip portion the protruding first lock portion is particularly well shielded from contact with surrounding tissue, reducing the possibilities for the clip abrading the surrounding tissue in use.

According to a second aspect of the present invention there is provided a surgical clip for clipping a tubular structure in vivo so as to ligate the tubular structure, the clip comprising:

first and second clip portions; and a hinge portion connecting said clip portions together to enable said clip portions to be hinged together from an open clip condition to at least one closed clip condition so as to ligate a tubular structure placed between said clip portions;

wherein each of the clip portions has a clamping surface which is arranged to be positioned in opposition to the clamping surface of the other clip portion in the closed clip condition; and wherein the hinge portion has a pivot axis about which the first and second clip portions are hinged and in said closed clip condition the maximum dimension of the clip in the direction of that hinge axis is at least 0.25 times the maximum dimension of the clip in a direction orthogonal to the hinge axis, which orthogonal direction is generally parallel to said opposed clamping surfaces in said closed clip condition.

A plurality of clips may be provided in a variety of different sizes to cater for the clipping of tubular structures of different sizes.

Although the majority of the clip may be made of metal, for example stainless steel or titanium, advantageously at least a majority of the clip structure is non-metallic, for example being made of nylon or polydiaxonone, so as to render the clip substantially invisible during magnetic resonance imaging (I) or computerised tomography (CT) scanning, whilst still remaining visible to ultrasound.

Advantageously, the clip is so constructed and arranged that, in the (or each) closed clip condition, at least part of one of the clamping surfaces is spaced apart from at least part of the other of the clamping surfaces. In such a situation the size of the spacing could be made to be appropriate to the size of the tubular structure to be ligated. This, and the provision of a lock for locking the clip portions together in the closed clip condition, may help to reduce the possibility of the tubular structure slipping out from the clip once the clip is in its closed clip condition. Improving the non-slip nature of the clip provides the surgeon with improved peace of mind, enabling the clips to be placed very close together on a vessel to be divided in continuity. By minimising this distance some of the abovementioned problems with prior art clips, such as the aforementioned neovascularization risk, can be fully or partially solved.

A cartridge or magazine may be provided comprising a plurality of the clips, with the clips being removably provided in a cartridge or magazine structure.

Alternatively or additionally, the surgical clip may be provided in combination with a surgical clip application device, which device is operable to apply the clip around the tubular structure to be ligated and to switch the clip from its open clip condition to its closed clip condition so as to ligate the tubular structure.

The clip, cartridge or magazine or application device/clip combination may advantageously be provided in a sterile container, ideally with any unused contents of the sterile container being disposed of after a single patient procedure.

According to a further aspect of the present invention there is provided a method of ligating a tubular structure comprising:

providing a surgical clip in accordance with the first aspect of the present invention;

applying the clip in said open clip condition to the tubular structure to be ligated, with the tubular structure extending between the open clip portions; and hinging the clip portions together about the hinge portion so as to convert the clip from its open clip condition to its closed clip condition, thereby to ligate the tubular structure.

Embodiments of apparatus in accordance with the present invention will now be described, by way of example only, with reference to the accompanying drawings, in which.

FIG. 4 illustrates a first embodiment of surgical clip for use in clipping a tubular structure in vivo so as to ligate the tubular structure. The clip 5 comprises a first clip portion or half 6 and a second clip portion or half 7. A hinge portion 8 connects the clip portion 6, 7 together. FIG. 4a shows the clip in an open condition, with the clip portion 6, 7 angled at right angles to one another, with a tubular structure 9, such as a vein or vessel, placed between the open clip portions. The hinge portion 8 enables the clip portion 6, 7 to be closed together to assume the closed clip condition shown in FIG. 4b, in which condition the tubular structure 9 is compressed so as to ligate it.

Figure 6A:
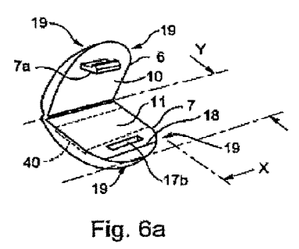
FIG. 6a is a perspective view, to a different scale, of the clip of FIG. 5a (with the vessel removed for clarity)
Figure 6B:
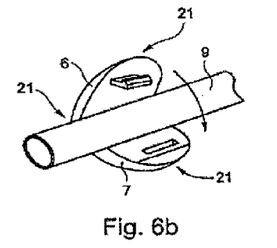
FIG. 6b is a similar view to that of FIG. 6a, but additionally showing the vessel to be ligated received in the clip.
Figure 6C:
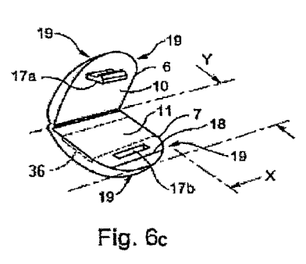
FIG. 6c is a perspective view, to a different scale, of the clip of FIG. 5a (with the vessel removed for clarity) showing surface undulation.
Figure 6D:
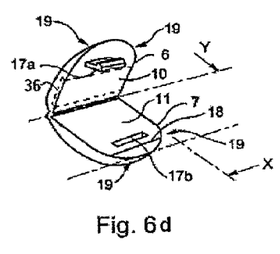
FIG. 6d is a perspective view, to a different scale, of the clip of FIG. 5a (with the vessel removed for clarity) showing surface undulation.
Figure 6E:
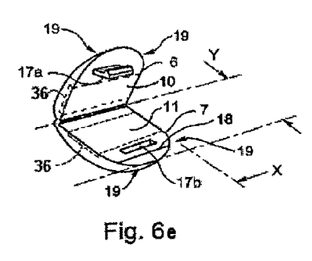
FIG. 6e is a perspective view, to a different scale, of the clip of FIG. 5a (with the vessel removed for clarity) showing surface undulation.

As will be described below in conjunction with FIG. 6, the clip 5 has a substantially smooth external profile in its closed clip condition so as to reduce the possibility of the clip eroding surrounding structures. In addition, the absence of rough or sharp ends or edges to the exterior of the clip 5 should be noted.

Figure 4A:
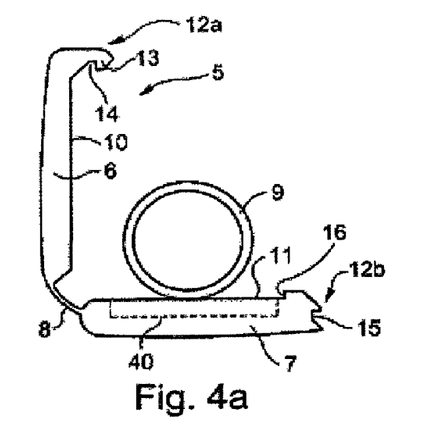
FIGS. 4a and 4b are enlarged end elevations of a first embodiment of surgical clip, showing the clip (with a vessel received therein) in open and closed conditions respectively.
Figure 4B:
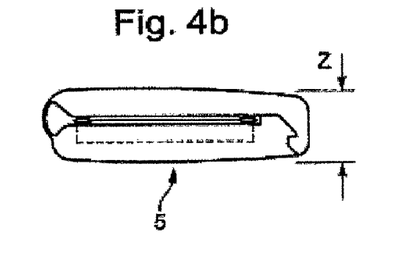
Figure 4C:
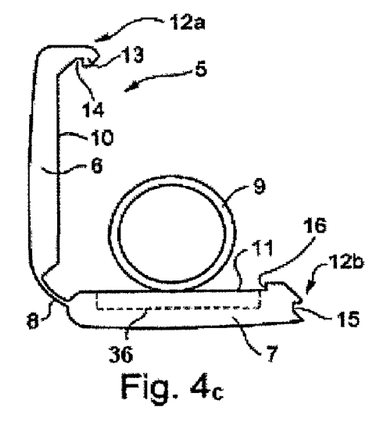
FIGS. 4c, 4d, and 4e are enlarged end elevations of a first embodiment of a surgical clip, showing the clip (with a vessel received therein) in an open condition having surface undulation.
Figure 4D:
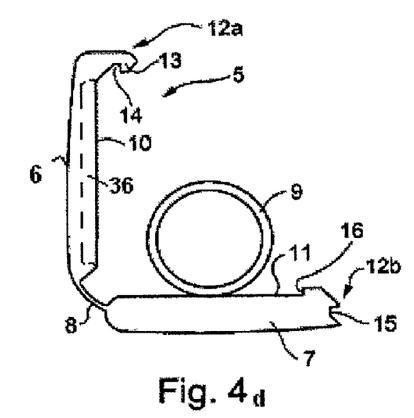
Figure 4E:
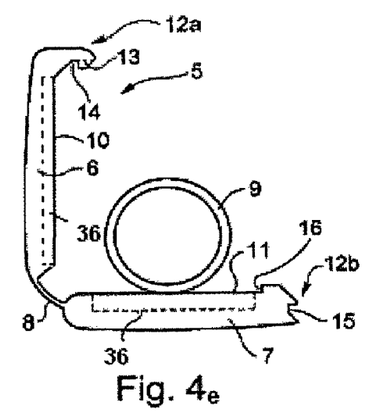

The first clip portion 6 is provided with a planar clamping surface 10 and the second clip portion 7 is provided with a planar clamping surface 11, which clamping surfaces 10, 11 are arranged to be positioned opposite to one another, with their planar surfaces generally parallel in the closed condition of the clip, as shown in FIG. 4b. Although shown as being planar, the clamping surfaces 10, 11 need not be planar. Furthermore, one or more of the clamping surfaces 10, 11 may additionally be provided with surface undulation 36 (See FIGS. 4c, 4d, 4e, 5c, 5d, 5e, 6c, 6d, 6e, 11C, 11D, 11E) so as to enhance gripping of the tubular structure 9. In addition, as described in more detail below, one or more of the clamping surfaces may be provided with a pad of cushioning material.

The clip 5 is provided with a lock 12 for locking the clip portions 6, 7 together in the closed clip condition. The lock 12 is provided on the opposite side of the clip 5 to the hinge portion 8 so that, as shown in FIG. 4b, the tubular structure 9 ligated by the clip is positioned between the hinge portion 8 and the lock 12.

The lock comprises a first lock portion 12a provided on the first clip portion 6 and a second lock portion 12b provided on the second clip portion 7. The first lock portion 12a protrudes beyond the clamping surface 10 of the first clip portion 6 in a direction substantially perpendicular to that clamping surface 10. The distal portion 13 of the first lock portion 12a is larger than the more proximal portion 14 of the protruding first lock portion, thereby forming a barb-like member. The second lock portion 12b is provided on the outside edge of the second clip portion 7 and includes a barb which forms a recess 15 into which the barb 13 of the first lock portion 12a "snaps" (as shown in FIG. 4b) in the closed clip condition. The second clip portion 7 is thus provided with an external, open recess to receive the first lock portion 12a in the closed clip condition, to shield the distal end from projecting into surrounding tissue structures. It will, however, be noted that in the closed clip condition one side of the distal end of the first lock position 12a is nonetheless still exposed to contact surrounding tissue structures.

The first and second locking portions 12a, 12b are arranged to function as a permanent lock to prevent the clip, once in its closed clip condition, from being opened to be returned to its open clip condition. In this way the clip portions can be reliably locked together. A further benefit of the illustrated construction of lock is that it provides a good feel on closure, snapping shut, giving the surgeon confidence that the lock has been locked securely.

The second clip portion 7 is provided with a lip or step 16 of predetermined height. The step 16 provides a "stand-off" between the clamping surfaces 10, 11 in the closed clip condition so as to accommodate the wall of the tubular structure 9, as best seen in FIG. 4b. The height of the step 16, and thus the size of the spacing between the clamping surfaces 10, 11, is chosen to be appropriate to the size and wall thickness of the tubular structure to be ligated and/or to the overall dimension of the clip. For example, the size of the standoff might be between 0.1-1 mm. A clip for use in ligating a small vein of 1-2 mm diameter might itself have a height ("Z") of approximately 3-4 mm, with a "stand-off" (represented by step 16) of approximately 0.3-0.5 mm. The intention is that when the clip is hinged to its closed condition the enclosed tubular structure 9 will be well compressed and flat and have no tendency to slip or move relative to the clip structure. The reliability and non-slip nature of the clip is intended to allow a pair of clips to be placed as close together as possible as will still allow a knife to pass between them. An advantage of this will be to help minimise the problem of neovascularization discussed above.

Figure 5A:
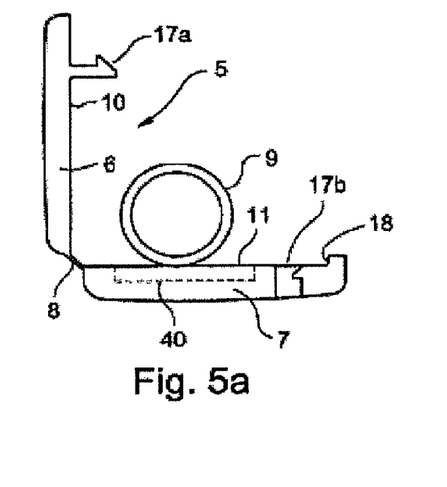
FIGS. 5a and 5b are enlarged end elevations of a second embodiment of surgical clip, showing the clip (with a vessel received therein) in open and closed conditions respectively.
Figure 5B:
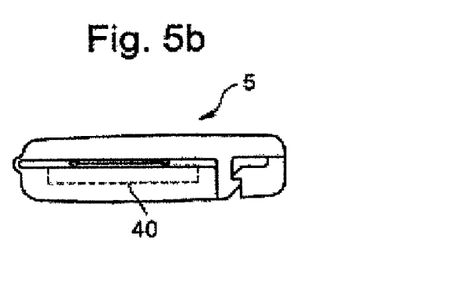
Figure 5C:
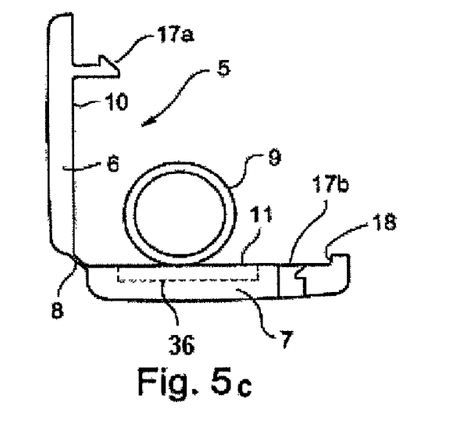
FIGS. 5c, 5d, and 5e are enlarged end elevations of a second embodiment of a surgical clip, showing the clip (with a vessel received therein) in an open condition having surface undulation.
Figure 5D:
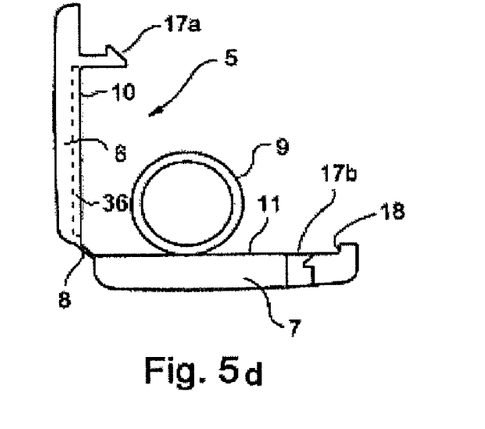
Figure 5E:
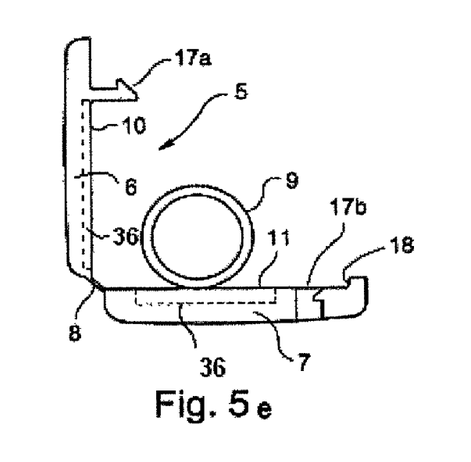

The second embodiment of clip, illustrated in FIGS. 5a and 5b, is generally similar in construction and operating principle to the first embodiment illustrated in FIGS. 4a and 4b. As a consequence, where constructional details are similar, like reference numerals have been employed. The main area of difference is in the form of the lock 17 and the step 18. One such difference is that the distal end of the first lock portion 17a is internally received within the body of the second clip portion.

In the FIG. 5 embodiment the first lock portion 17a still protrudes from the first clip portion's clamping surface 10, but is moved in from the edge of the first clip portion. The second lock portion 17b takes the form of a hole in the second clip portion's clamping surface 11, which hole extends through the full depth of the body of the second clip portion 7 and opens through the underside of the clip portion. As a consequence, the first lock portion is surrounded in the closed clip condition and is shielded from substantial contact with the surrounding tissue structures. This is thought to be preferable to the arrangement illustrated in FIGS. 4a and a 4b because it eliminates the possibility of the first lock portion 17a abrading and irritating the surrounding tissue structures.

Each of the first and second lock portions 17a, 17b comprises a single barb, which barbs cooperate in the closed clip condition so as to lock the two clip portions 6, 7 together, as illustrated in FIG. 5b. As can also be seen from that figure, the step 18 functions to provide the above-discussed "stand-off".

FIGS. 6a and 6b show how the first and second locking portions 17a, 17b do not extend across the full width of the clip. FIG. 6a shows the second embodiment of clip in its open clip condition, prior to application to the tubular structure to be ligated. FIG. 6b shows the clip applied to the tubular structure 9 to be ligated, with the tubular structure extending between the open clip portions 6, 7.

The curved nature of the first and second clip portions 6, 7 is apparent from FIGS. 6a, 6b. The heavily radiused corners, referenced 19, contribute to the substantially smooth external profile of the clip in its closed clip condition, thereby reducing the possibility of the clip eroding surrounding structures in vivo.

A significant difference from prior art, metal clips is in the aspect ratio of the clip. In FIG. 6a the pivot axis 20 of the hinge portion is illustrated. The maximum (width) dimension of the clip in the direction of that hinge axis is referenced "X". The maximum dimension of the clip in any direction orthogonal to the hinge axis 20 is the length dimension referenced "Y". In the closed clip condition this maximum (length) dimension is measured generally parallel to the closed clamping surfaces 10, 11. In contrast, the (height) dimension "Z" of the clip (see FIG. 5b) in the closed clip condition is comparatively small.

In the closed clip condition the maximum dimension "X" of the clip in the direction of the hinge axis 20 is, as shown, preferably at least 0.25 (more preferably at least any one of 0.5, 0.6, 0.7, 0.8 or 0.9) times the maximum dimension of the clip in all directions orthogonal to the hinge axis, including the largest dimension "Y" of the clip in the length direction. It will be appreciated that once "X" is approximately equal to "Y", the clip will have a shape very suitable for receipt in the body. As a consequence, the ends 21 of the clip, when in its closed clip condition, are blunt. This contrasts with prior art metal clips where the width dimension of the clip is commonly of the order of 1/10 to 1/5 of the length dimension of the clip, leading to the clip (in its closed condition) having sharp ends, which enable the prior art clips to be felt through the skin when used close to the skin surface and/or risk adjacent structures being eroded by the comparatively sharp ends of the clip.

It will be appreciated that the larger is the width "X" at the clip, the greater will be the area of the clamping surfaces 10, 11 available to clamp and ligate the vessel 9. For a given degree of vessel compression, increasing the clip-to-vessel contact area generally improves clip security and reduces the likelihood of the clip damaging the vessel wall.

Figure 7A:
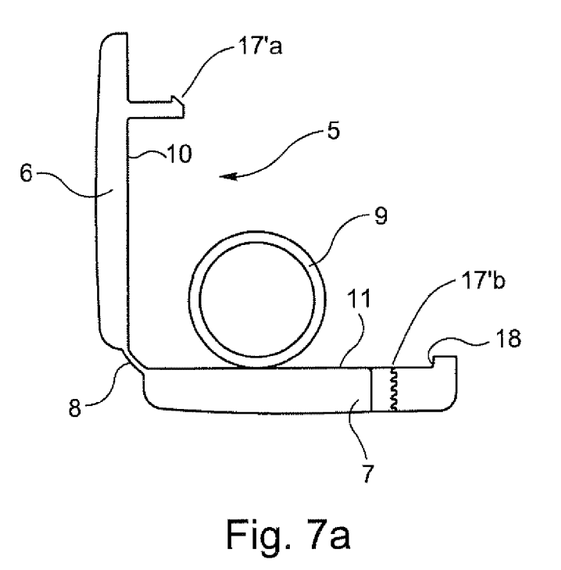
FIGS. 7a and 7b are enlarged end elevations of a third embodiment of surgical clip, showing the clip (with a vessel received therein) in open and closed conditions respectively.
Figure 7B:
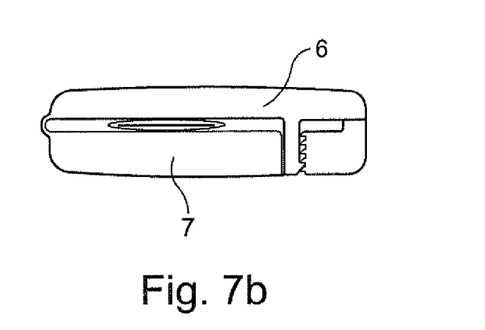
Figure 7C:
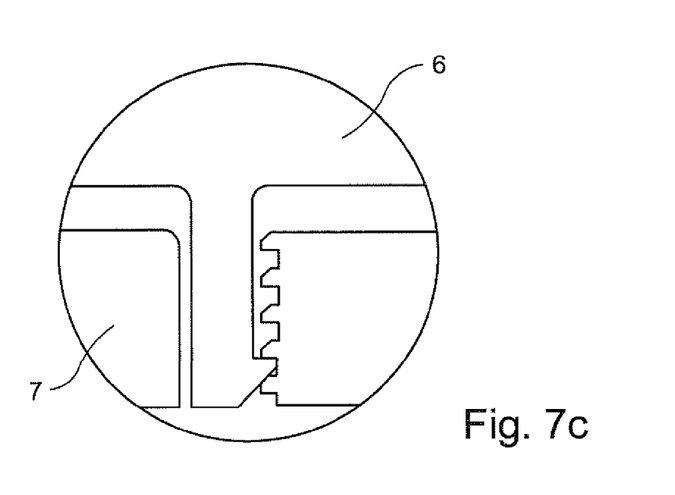
FIG. 7c is an enlargement of the lock area shown in FIG. 7b.

The third embodiment of clip, illustration in FIGS. 7a-7c, is generally similar in construction and operating principle to the second embodiment illustrated in FIGS. 5 and 6. As a consequence, where constructional details are similar, like reference numerals have been employed. The area of difference is in the form of the lock 17'.

The first lock portion 17'a in FIG. 7 is generally similar to the first lock portion 17a in FIGS. 5 and 6, in that it protrudes from the first clip portion's, clamping surface 10 and comprises a single barb at its distal end. The construction of the second lock portion 17'b is, however, different from the second lock portion 17b in FIG. 6, in that it comprises five barbs, defining therebetween four barb-receiving recesses, thereby providing a choice of four different closed clip conditions or positions. This can have advantages in allowing a single construction of clip to be used to ligate vessels of a range of different sizes and thicknesses and/or with an unknown level of 'substance' enhanced by a disease process affecting the vessel. FIGS. 7b and 7c illustrate a closed clip condition representative of the maximum degree of closure of the four available levels of closure. Additionally, this arrangement provides a good feel for the surgeon. The multiple barbs of the second lock portion 17'b will cause the lock portions to function like a ratchet. As the clip is hinged from its open clip condition (FIG. 7a) to the illustrated one of the closed clip conditions (FIGS. 7b and 7c), the barb of the first lock portion 17'a will sequentially ratchet through the four barb-receiving recesses, which ratchet action may be felt by the surgeon through the clip application device (not shown) and/or provide a clicking sound, providing the surgeon with reassurance that the lock is functioning correctly.

It will be appreciated that if the vessel 9 to be ligated is bigger, or more diseased, than that shown in FIG. 7, it may be necessary and/or desirable to close the clip only so far as one of the other three available closed clip conditions (not shown).

It will also be appreciated that the first lock portion 17'a may be provided with more than one barb, so that when in a said closed clip condition a plurality of barbs of the first lock portion 17'a are in barb-to-barb contact with a plurality of barbs of the second lock portion 17'b. Increasing the number of contact points between the two lock portions 17'a, 17'b can enhance locking security. It will also be appreciated that numbers of barbs other than four may be employed.

Finally, it should be noted that in the fully closed clip condition illustrated in FIGS. 7b and 7c, the distal end of the projection of the first locking portion 17'a is arranged not to extend beyond the underside of the second clip portion 7 so as not to disrupt the generally smooth profile of the undersurface of the second clip portion 7.

In addition, the fact that the projection of the first locking portion 17a is internally received within the body of the second clip portion 7 provides the same benefits described above in relation to the FIGS. 5a and 5b embodiments.

Figure 8A:
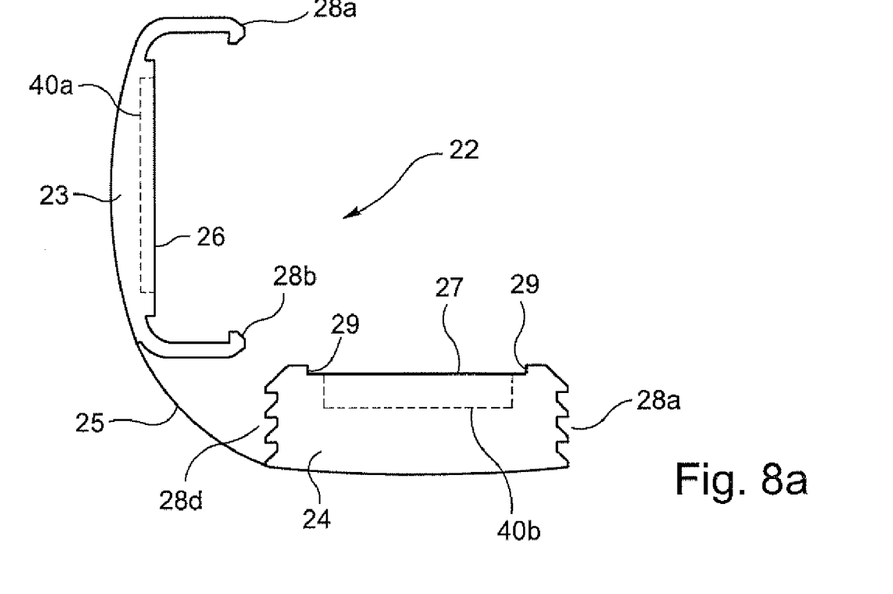
FIG. 8a is an enlarged end elevation of a fourth embodiment of clip shown in its open clip condition.
Figure 8B:
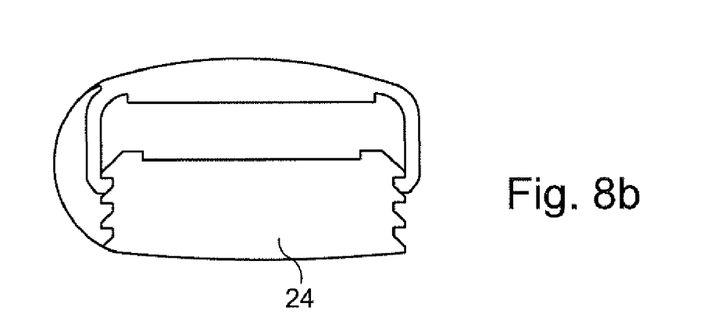
FIGS. 8b and 8c show the clip of FIG. 8a in two different ones of a plurality of closed clip conditions.
Figure 8C:
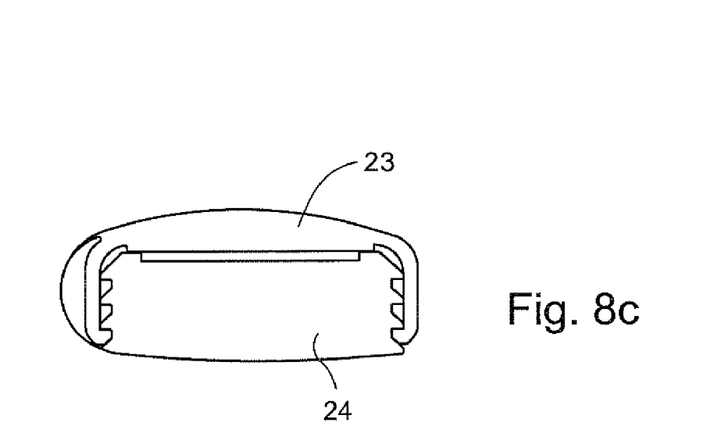

FIGS. 8a-c illustrate the closing sequence of a fourth embodiment of clip 22, with the tubular structure to be ligated omitted for reasons of clarity. In common with the earlier embodiments, the clip 22 comprises first and second clip portions 23, 24, connected by a hinge portion 25. As in the earlier embodiments, the clamping surfaces 26, 27 of the first and second clip portions 23, 24 are planar.

This fourth embodiment of clip is, like the third embodiment of clip, intended to be able to ligate tubular structures of a wide range of different diameters, through the ability of its lock 28 to be able to lock the first and second clip portions 23, 24 together in a plurality of different closed clip conditions. FIG. 8b illustrates a first closed clip condition. FIG. 8c illustrates a second closed clip condition. From the following description of the lock it will be apparent that locking can also take place in closed clip conditions between these first and second closed clip conditions. A pair of first lock portions 28a, 28b are provided on the first clip portion and a pair of second lock portions 28c, 28d are provided on the second clip portion 24. The first lock portions 28a, 28b each comprise a projection with a single barb at its distal tip. The second lock portions 28c, 28d each comprise a plurality of barbs, with barb-receiving recesses formed therebetween.

By hinging the first and second clip portions 23, 24 together around the hinge portion 25 and pressing the first clip portion 23 down onto the second clip portion 24, the barbs of the first lock portions 28a, 28b can be made to engage the first (uppermost as drawn) recesses of the second lock portions 28c, 28d. If the tubular structure to be ligated is suitably large and/or has a large wall thickness, the first closed condition illustrated in FIG. 7b may be sufficient to fully ligate the tubular structure, such that the first and second clip portions 23, 24 need not be pressed together further. If, however, the tubular structure (not shown) is smaller, the two clip portions 23, 24 may be pushed together further, either finally to reach the second closed clip condition shown in FIG. 7c, or an intermediate closed clip condition (not shown) between the FIG. 7b and FIG. 7c first and second closed clip conditions. It will be noted that the second clip portion 24 is provided with a step 29 at either end of its clamping surface 27 to provide a "stand-off" in the manner discussed above in conjunction with the first and second clip embodiments.

If, as intimated above, the condition illustrated in FIG. 8b is the final, closed clip condition, it will be appreciated that the lower, unshielded barbs of the first lock portion 28a will be exposed to contact with surrounding tissue. This is not as desirable as the condition shown in FIG. 8c, in which the closed clip presents a smoother external profile to the surrounding tissue structures.

By way of explanation, in this specification, when the term 'closed clip condition' is used it can mean either the sole available condition in which the clip is closed, for examples as in FIGS. 4-6 and 9-11, or any one of a plurality of available conditions in which the clip is closed, for example as in FIGS. 7 and 8.

Providing the second lock portions 28c, 28d with plural barbs, and plural recesses therebetween, provides a ratchet-like arrangement, thereby accommodating vessels of different sizes and/or 'substances'. Although the first lock portions 28a, 28b are each shown as comprising only a single barb, it will be appreciated that multiple barbs could equally well be provided to increase the number of barb-to-barb contacts in the final closed clip condition. In the same way, the first embodiment of FIG. 4 could readily be modified to make one or both of its first and second lock portions 12a, 12b multi-barbed.

Figures 9A, 9B:
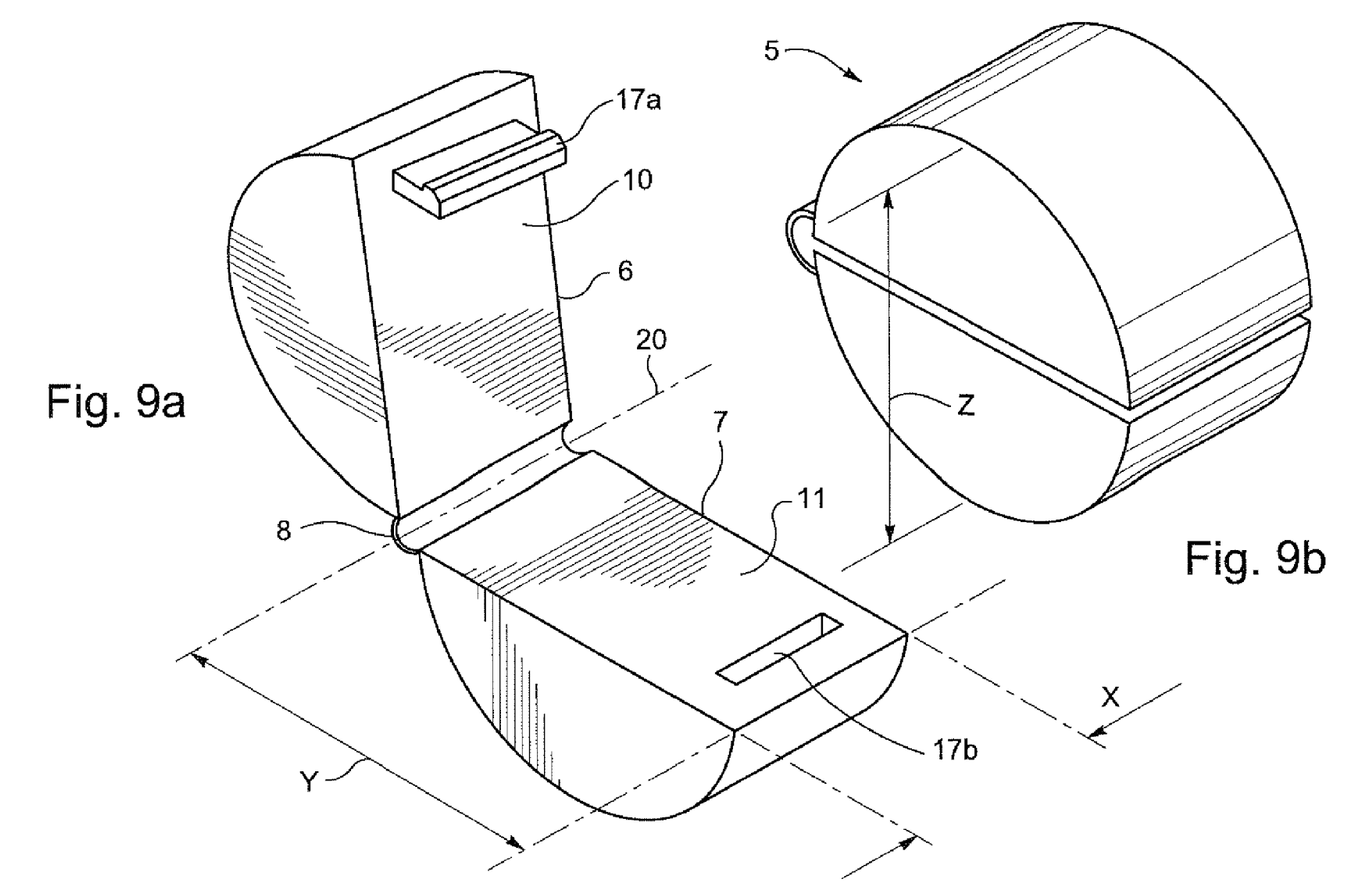
FIGS. 9a and 9b are perspective views of a fifth embodiment of clip, showing the clip in open and closed conditions respectively.

FIGS. 9a and 9b are perspective views of a fifth embodiment of clip, showing the clip in open and closed conditions respectively. Apart from its aspect ratio, and the absence of a step to provide a stand-off, the fifth embodiment of clip is generally similar in construction and operating principal to the second embodiment of clip illustrated in FIGS. 5 and 6. As a consequence, where constructional details are similar, like reference numerals have been employed.

In contrast to the second embodiment of clip, the aspect ratio of the sixth embodiment of clip is somewhat different. Referring to FIGS. 4 and 5, in the second embodiment of clip where the width, length and height of the clip are referenced "X", "Y" and "Z" respectively, the height "Z" of the closed clip is fairly small and is smaller than the width "X" and length "Y" of the clip. As shown in FIG. 9, this need not however, be the case. In FIG. 9 the height "Z" of the closed clip is substantially larger. In FIG. 9 the height "Z" is larger than the width "X" of the clip and generally equal to the length "Y" of the clip. As will be appreciated from FIG. 9b, the generally cylindrical nature of the fifth embodiment of clip, when in its closed clip condition, means that the length "Y" and height "Z" of the clip will be approximately equal to one another.

It will, however, be noted that, as in the earlier embodiments, in the fifth embodiment of clip the maximum dimension of (width "X") of the clip in the direction of hinge axis is over 0.25 times the maximum dimension (length "Y") of the clip in the direction orthogonal to the hinge axis, which orthogonal direction is parallel to the opposed clamping surfaces in the closed clip condition illustrated in FIG. 9b.

Although in this illustrated embodiment the maximum width of the clip is coincident with the hinge axis, the width need not be measured at the hinge axis but could be displaced therefrom, albeit with the measurement being in a direction parallel to the hinge axis.

Although in FIG. 9 the first and second lock portions 17a, 17b are shown to have the same constructions as the first and second lock portions of the second embodiment of clip illustrated in FIGS. 6a and 6b, the comments above concerning how those locking portions might be modified (to make one or both of the locking portions include a plurality of barbs) apply equally here.

Figure 10:
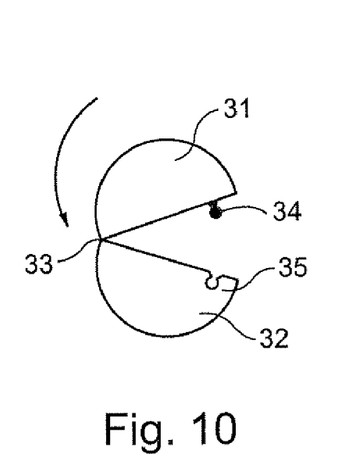
FIG. 10 is an enlarged, schematic, end elevation of a sixth embodiment of clip in an open clip condition.

FIG. 10 illustrates a sixth embodiment of clip 30 in which the first and second clip portions 31, 32 are both either generally hemispherical or hemioval in shape, such that when the clip portions are hinged around the hinge portion 33 to adopt a closed clip condition (not shown) the closed clip has a substantially smooth external (generally spherical or oval) shape. In this embodiment the lock takes the form of a press stud arrangement, in which the distal end of the first lock portion protruding from the first clip portion has a generally spherical head 34 and the second lock portion provided in the second clip portion 32 takes the form of a recess 35 (shown in dotted lines) having an opening slightly smaller in size than the generally spherical head 34 so that the first and second lock portions are required to deform elastically to enable them to be locked together. In this embodiment, in which the shape of the clip in its closed condition is generally spherical, the width, length and height of the clip are all equal.

Figure 11A:
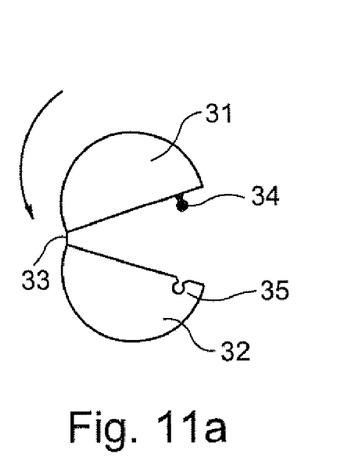
FIGS. 11a and 11b are schematic, enlarged, end elevations of a seventh embodiment of clip in open and closed clip conditions respectively.
Figure 11B:
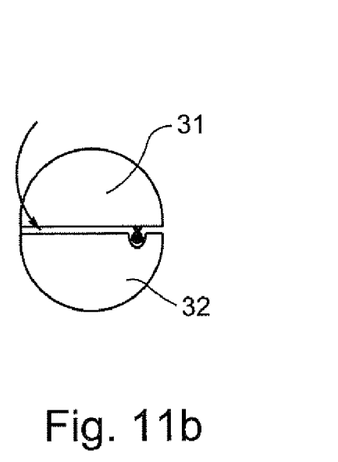
Figure 11C:
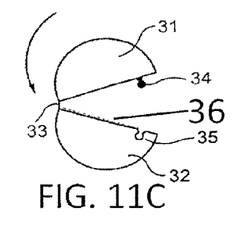
FIGS. 11C, 11D, and 11E show this embodiment with surface undulations.
Figure 11D:
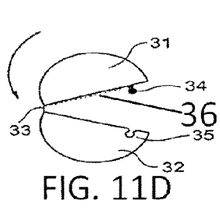
Figure 11E:
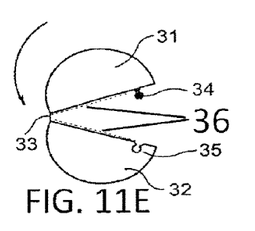

FIGS. 11a and 11b illustrate a seventh embodiment of clip which is identical to the sixth embodiment of clip illustrated in FIG. 10, except that in the seventh embodiment the hinge portion 33 is elongated so as to provide a "stand-off" gap as shown in FIG. 11b.

From the range of lock constructions illustrated, it will be appreciated that other forms of lock may be provided. For example, any form of lock that securely locks when the clip is in the closed clip condition should be appropriate. Particularly preferred are ones that snap shut automatically, reliably and with a good "feel".

In each of the aforementioned embodiments of clip, one or both of the first and second clip portions may have a non-homogeneous construction, for example with the part of at least one clip portion which forms the substantially smooth external profile being made of a first, hard material and the part of the clip portion which forms the clamping surface being made of a second, softer material. To illustrate this, in FIGS. 4a and 4b the second clip portion is shown as being optionally provided with a pad 40 (in broken lines) of the second, softer material inset into the internal surface of the second clip portion 7 to form a cushioned central portion to the clamping surface 11. This pad 40 may, for example, have a hardness generally similar to that of soft silicone, and may have been moulded in situ on the material forming the remainder of the clip using a multi-stage moulding process. In such a situation the material of the remainder of the clip may, for example, have a hardness generally similar to that of hard polypropylene. This non-homogeneous construction for the clip means that the main structure of the clip can have the required strength, whereas at least one of the clamping surfaces for contact with the tubular structure can be cushioned so as to deform more exactly to the vessel being clamped, thereby improving clip security, and to avoid cutting through the vessel.

It will be appreciated that other biocompatible plastics materials may be used instead for the clip. Plastics materials are cheap and easily mouldable.

Alternatively, some or all of the clip may be made of metal, for example stainless steel or titanium, with or without an inset pad of cushioning material.

FIGS. 5a-6a also show, in broken lines, a pad 40 of cushioning material optionally provided in the second clip portion 7. As can be seen, the pad 40 can extend the full width of the second clip portion 7. Alternatively, it may stop short of the full width (not shown).

To illustrate how both of the first and second clip portions (23, 24) might optionally be provided with a pad 40 of cushioning material, two such pads 40a, 40b have been illustrated in FIG. 8a in broken lines.

Although only illustrated in conjunction with selected embodiments, the principles of non-homogeneous construction and/or the provision of cushioning material apply equally to all embodiments.

As described below, it is envisaged that the aforementioned embodiments of clip would be applied to the tubular structure to be ligated using a specific application device or tool. The clips could be provided in a cartridge or magazine for serial application using an application device. Alternatively, the application device may be pre-loaded with a plurality of clips. The clips, cartridge or magazine or application device may advantageously be provided in a sterile container.

Figure 12:
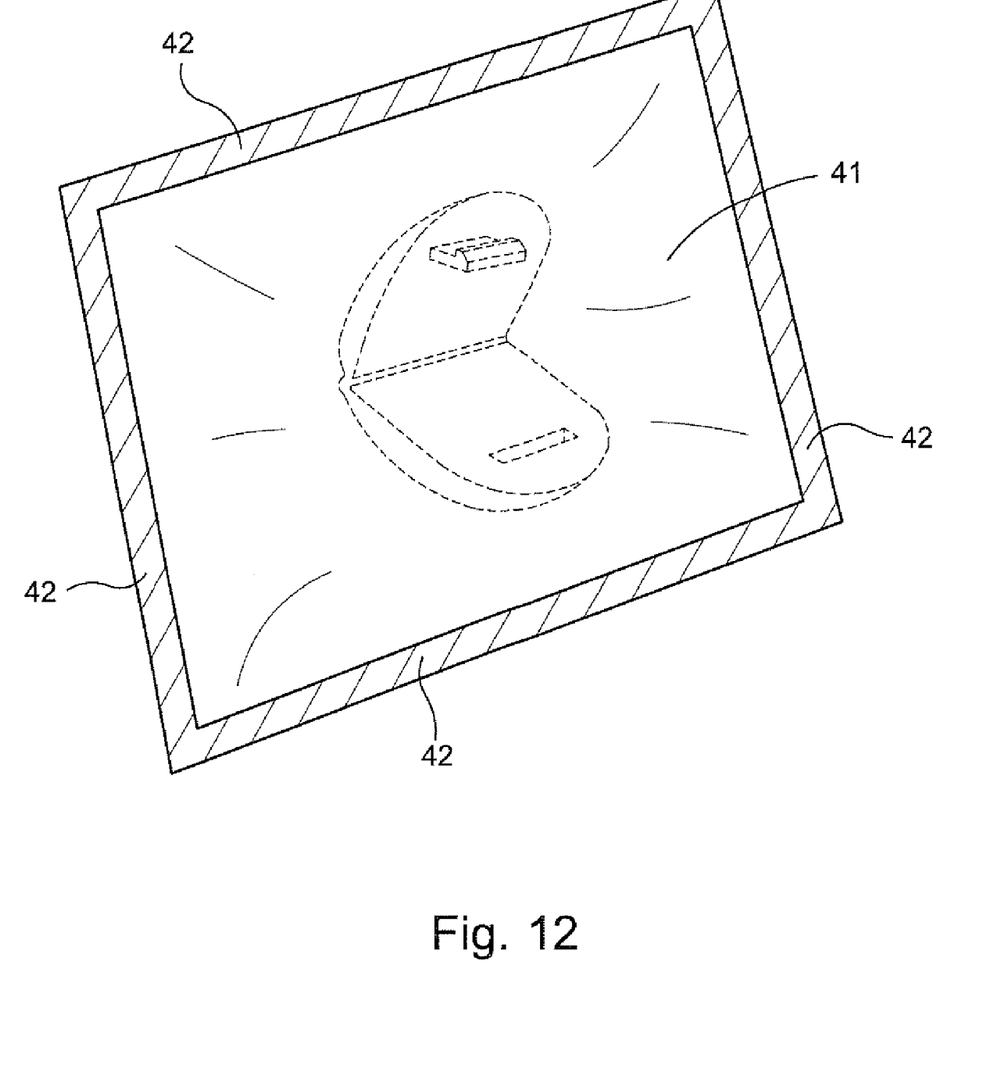
FIG. 12 is a perspective view of a clip in a sterile package.

The above-described embodiments of clip may be provided singly, and may for example be provided in a sterile container, such as an envelope at least a portion of which is transparent. FIG. 12 shows schematically a clip received in a sterile envelope 41 comprising two planar sheets heat sealed together around their peripheral edge 42, which envelope can be torn open by the surgeon prior to use of the clip.

Figure 13:
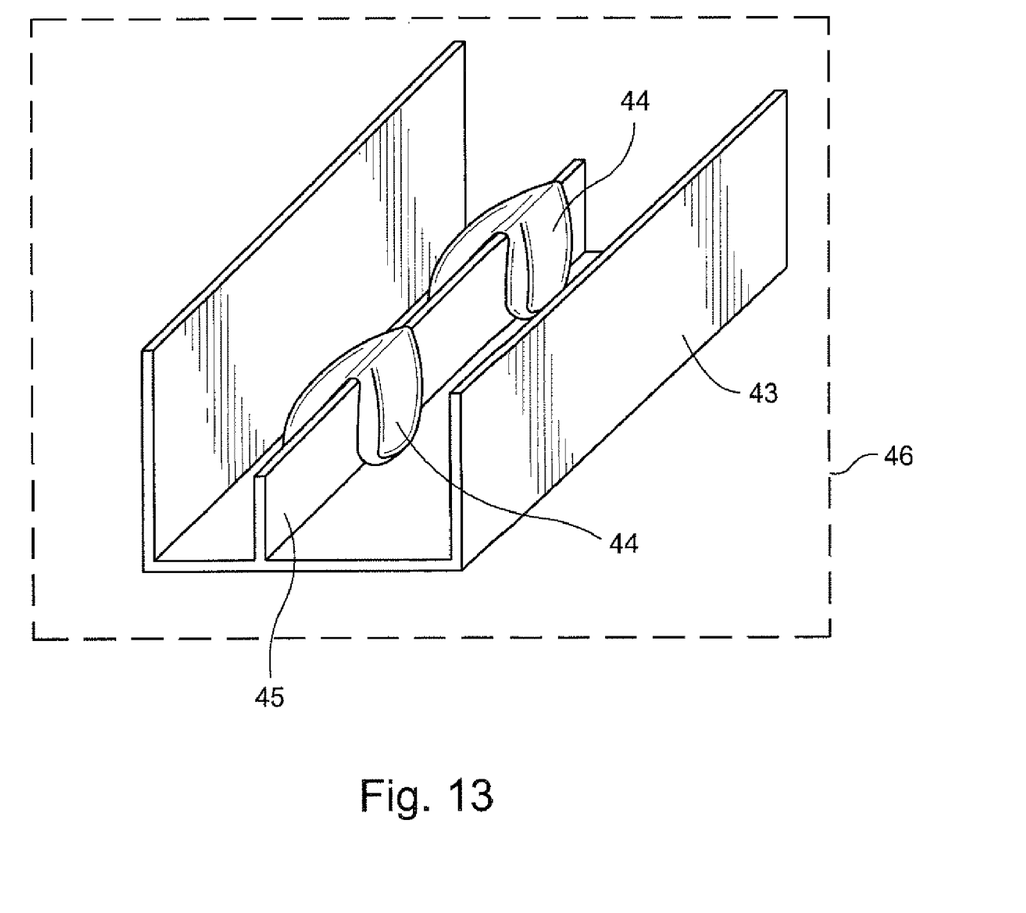
FIG. 13 is a perspective view of a plurality of clips in a cartridge or magazine packaged in a sterile package.

Rather than being provided singly, a plurality of clips may alternatively be provided in a cartridge or magazine structure from which they are removed prior to use. By way of example, FIG. 13 illustrates a portion of a cartridge or magazine structure 43 in which a pair of clips 44 are shown as being removably provided. In the illustrated arrangement the opposing clip portions are placed on either side of a central web 45 of the magazine structure. A form of catch (not shown) may be provided on the magazine structure so as to prevent the clips 44 from falling out of the structure, with the clips only parting company with the structure when removed therefrom by the surgeon. The square, shown in broken lines and referenced 46, denotes the outline of a sterile container in which the magazine structure 43 may be received, the sterile container having a construction similar, for example, to that described above in conjunction with FIG. 12.

Figure 14:
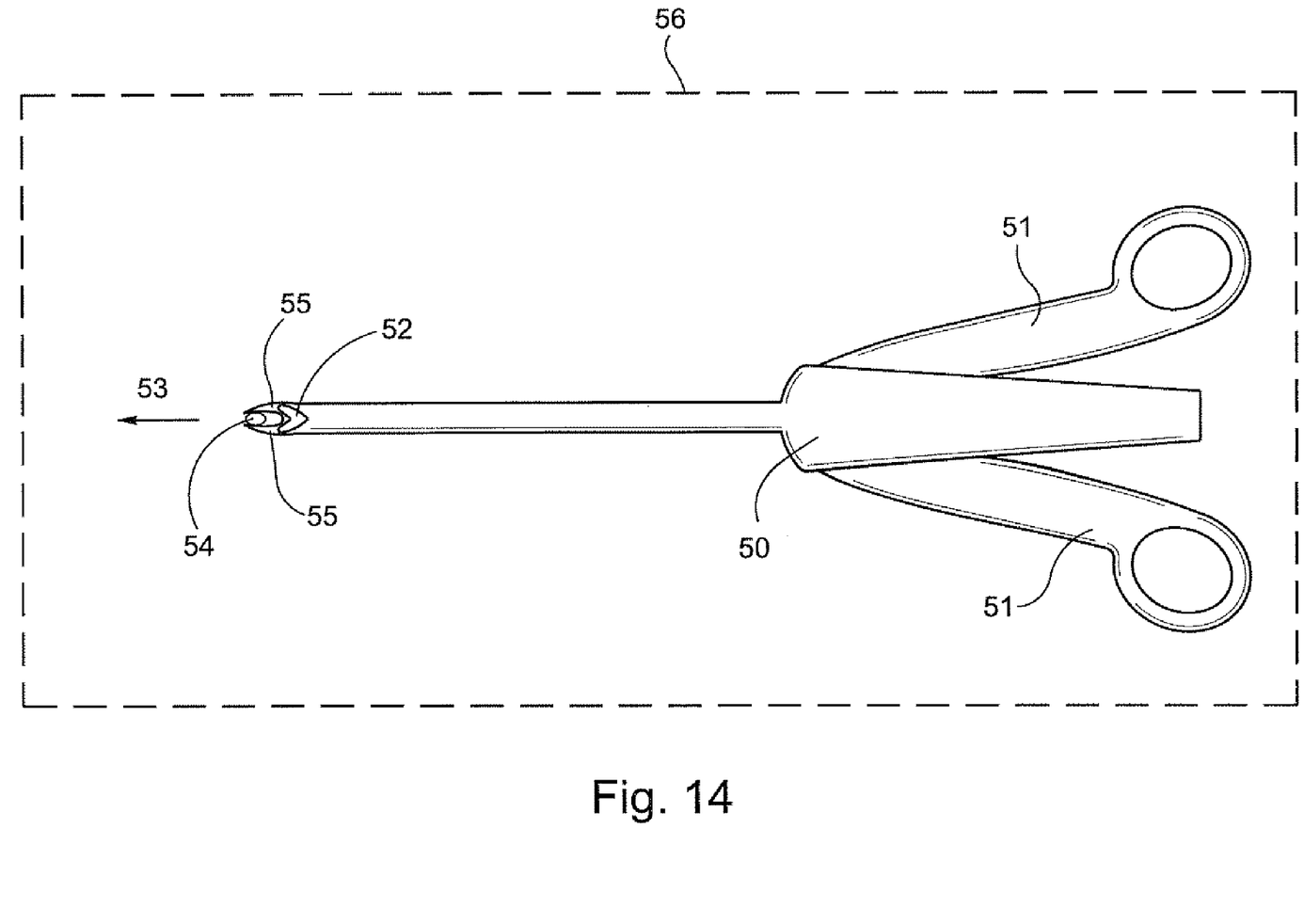
FIG. 14 is a top plan view of a clip application device in a sterile package.

FIG. 14 illustrates, schematically, an application device which is pre-loaded with a plurality of clips. At one end of the applicator device 50 there is provided a pair of handles 51 which, upon being squeezed together, cause a clip 52 to be displaced (in direction 53) from the opposite end of the device and squeezed together to lock together the clip portions. If, therefore, a vessel 54 to be ligated is positioned between the end prongs 55 of the device, a clip 52 may be clipped on to the vessel 54. The manner of operation of the applicator device could be generally similar to that of the PREMIUM SUR-GICLIP (Trademark) single use automatic clip application device manufactured by United States Surgical, a division of Tyco Healthcare Group LP. Such a device is described in U.S. Pat. Nos. 5,030,226; 5,197,970; 5,514,149; and 5,626,592, as well as in U.S. design Pat. Nos. 320,654 and 320,850, the contents of which documents are hereby incorporated by way of reference. The rectangle represented by broken lines 56 in FIG. 14 denotes a sterile container in which the application device 50 may advantageously be provided.

Four examples of the use of the above described embodiments of clip might include one or more of the following four applications.

1. In the groin dissection during varicose vein surgery, when all tributaries of the LSV/femoral vein have to be ligated and divided—here the new clip would be useful as its smooth surface would not cause potential problems of erosion/thrombosis in the femoral vein and the ability to minimum distance between cut ends of vessel would minimize neovascularization—perhaps the most common cause of recurrence.

2. In harvesting LSV for cardiac/peripheral bypass surgery, the new clips just below the skin surface, being smooth, would not cause discomfort to the patient as rough ended, flat clips as in use now might.

3. With a bleeding vessel at laparoscopic cholecystectomy e.g. the cystic artery, secure placement of a single new clip should prevent undue blood loss and instill confidence in the surgeon that the new clip is indeed secure and will not be dislodged with further dissection.

4. In the brain, clipping beri-aneurysms will be secure first time, with no possibility of slippage, in a difficult, tight, working environment. Post-procedure, when MRI/CT scanning might be necessary, if the clip is of a non-metallic substance, no artefact will be seen on scans.

The invention claimed is:
1. A surgical clip for ligating a tubular vessel in vivo, the clip consisting essentially of:
 a first clip portion comprising:
  a first external surface;
  a first clamping surface positioned on a surface of the first clip portion opposite of the first external surface;
 a second clip portion coupled to the first clip portion, comprising:
  a second external surface;
  a second clamping surface positioned on a surface opposite of the second external surface;
 a hinge portion coupling the first and second clip portions positioned at a first end of the first and second clip portions, comprising:
  a pivot axis about which the first and second clip portions are hinged such that the clip portions are configured to move from an open condition to a closed condition; and
 a lock for locking the clip portions together when in use such that the tubular vessel placed between the first and second clip portions is ligated, comprising:
  a first lock portion positioned proximate an end of the first clip portion opposite the hinge portion; and
  a second lock portion positioned proximate an end of the second clip portion opposite the hinge portion;
 wherein the first lock portion and the second lock portion are positioned to cooperate to lock the clip portions together during use;
 wherein at least one of the clamping surfaces comprises surface undulation and at least a portion of the surface undulation contacts the tubular vessel during use;

wherein the clamping surfaces and hinge portion are positioned such that the clamping surfaces are substantially parallel to one another when the tubular vessel is ligated during use;

means providing a stand-off gap between the clamping surfaces of at least 0.1 mm across the length of clamping surfaces in the absence of the tubular vessel when the clip is in the closed position;

wherein a first maximum dimension of the clip in a first direction is between about 0.25 and about 1.0 times a second maximum dimension of the clip in a second direction and wherein the first and second directions are orthogonal to each other and the first and second directions are parallel with the clamping surfaces when the clip is in the closed condition;

wherein in use the tubular vessel is accommodated when positioned between the first clamping surface and the second clamping surface;

wherein in use the clip has a substantially smooth substantially spherical or substantially ovoid external 3-dimensional shape that is substantially free of:
  i) external projections; and
  ii) rough or sharp ends or rough or sharp edges so as to reduce the possibility of the clip eroding tissue structures surrounding the clip in vivo.

2. The clip of claim 1 wherein the first direction is parallel to the pivot axis of the hinge portion.

3. The clip of claim 1 wherein the first maximum dimension of the clip is at least about 0.6 times the second maximum dimension of the clip.

4. The clip of claim 1 wherein the first maximum dimension of the clip is at least about 0.7 times the second maximum dimension of the clip.

5. The clip of claim 1 wherein the first maximum dimension of the clip is at least about 0.8 times the second maximum dimension of the clip.

6. The clip of claim 1 wherein the first maximum dimension of the clip is at least about 0.9 times the second maximum dimension of the clip.

7. The clip of claim 1 wherein the means providing a stand-off gap between the clamping surfaces comprises the hinge portion.

8. The clip of claim 7 wherein the tubular vessel to be ligated is positioned between the hinge portion and the lock portions during use.

9. The clip of claim 1 wherein the first lock portion protrudes from the first clip portion and wherein the second lock portion is positioned to couple to the first clip portion.

10. The clip of claim 1 wherein the first lock portion is provided with at least one barb and the second lock portion is arranged to receive the at least one barb so as to lock the clip portions together in use.

11. The clip of claim 1 wherein the first lock portion is provided with at least one barb and the second lock portion is arranged to receive the at least one barb so as to lock the clip portions together, wherein the second lock portion is provided with at least one barb, and wherein at least one of the first and second lock portions is provided with a plurality of barbs to function like a locking ratchet when the clip portions are hinged to the closed clip condition.

12. The clip of claim 11, wherein both of the first and second lock portions are provided with a plurality of barbs and wherein in use at least two barbs of the first lock portion are in contact with at least two barbs of the second lock portion to provide a plurality of barb-to-barb contacts.

13. The clip of claim 12 wherein the plurality of barbs enable the clip portions to be locked together in a plurality of different closed clip conditions during use, each different closed clip condition representing a different spacing between the clip portions, such that the clip can ligate tubular vessels within a range of different sizes.

14. The clip of claim 1 wherein in use the clip has a substantially spherical external shape.

15. The clip of claim 1 wherein both of the clip portions are substantially hemispherical in shape.

16. The clip of claim 1 wherein in use the clip has a substantially oval external shape.

17. The clip of claim 1 wherein both of the clip portions are substantially hemioval in shape.

18. The clip of claim 1 wherein the stand-off gap between the clamping surfaces in a closed clip condition is at least 0.3 mm.

19. The clip of claim 1 wherein the stand-off gap between the clamping surfaces in a closed clip condition is less than about 1 mm.

20. The clip of claim 1 wherein the clip structure is non-metallic.

21. The clip of claim 1 wherein the clip structure comprises polypropylene.

22. The clip of claim 1 wherein the clip structure comprises nylon.

23. The clip of claim 1 wherein the clip structure comprises polydiaxonone.

24. The clip of claim 1 wherein the clip is provided in a sterile container.

25. The clip of claim 1, wherein the stand-off gap between the clamping surfaces in a closed clip condition is less than about 0.5 mm.

26. The clip of claim 1 further comprising surface undulation on the first clamping surface and the second clamping surface.

27. A cartridge or magazine comprising a plurality of surgical clips having the construction claimed in claim 1, the surgical clips being removably provided in a cartridge or magazine structure and the cartridge or magazine being provided in a sterile container.

28. A combination of a surgical clip application device and at least one surgical clip having the construction claimed in claim 1, wherein the application device is operable to apply the at least one clip around a tubular vessel to be ligated and to switch the at least one clip from its open clip condition to a closed clip condition so as to ligate the tubular vessel.

29. The combination of claim 28, wherein the application device is pre-loaded with a plurality of the clips and is provided in a sterile container.

30. A method of ligating a tubular vessel, in vivo, comprising:
  providing a surgical clip as claimed in claim 1;
  applying the clip in the open clip condition to the tubular vessel to be ligated, with the tubular vessel extending between the open clip portions;
  arranging the clip such that the hinge is positioned on a first side of the tubular vessel and the lock is positioned on a second side when the lock is engaged; and
  engaging the lock to lock the clip portions together.

31. A method for ligating a blood vessel in vivo, comprising:
  providing a surgical clip consisting essentially of:
    a first clip portion comprising:
      a first external surface;
      a first clamping surface positioned on a surface of the first clip portion opposite of the first external surface;
    a second clip portion coupled to the first clip portion, comprising;
      a second external surface;
      a second clamping surface positioned on a surface opposite of the second external surface;

a hinge portion coupling the first and second clip portions positioned at a first end of the first and second clip portions, comprising:
    a pivot axis about which the first and second clip portions are hinged such that the clip portions are configured to move from an open condition to a closed condition; and
a lock for locking the clip portions together when in use such that the blood vessel placed between the first and second clip portions is ligated, comprising:
    a first lock portion positioned proximate an end of the first clip portion opposite the hinge portion; and
    a second lock portion positioned proximate an end of the second clip portion opposite the hinge portion;
    wherein the first lock portion and the second lock portion are positioned to cooperate to lock the clip portions together during use;
    wherein at least one of the clamping surfaces comprises surface undulation;
    the hinge portion provides a stand-off gap between the clamping surfaces of at least 0.1 mm across the length of clamping surfaces in the absence of the blood vessel when the clip is in the closed position;
    wherein a first maximum dimension of the clip in a first direction is between about 0.25 and about 1.0 times a second maximum dimension of the clip in a second direction and wherein the first and second directions are orthogonal to each other and the first and second directions are parallel with the clamping surfaces when the clip is in the closed condition;
positioning the surgical clip proximate the blood vessel;
applying the clip in the open clip condition to the blood vessel to be ligated, with the blood vessel extending between the open clip portions;
arranging the clip such that the hinge is positioned on a first side of the blood vessel and the lock is positioned on a second side when the lock is engaged; and
engaging the lock to lock the clip portions together; and thereby ligating the blood vessel;
wherein at least a portion of the surface undulation contacts the blood vessel during use;
wherein during use the first clamping surface and the second clamping surface are substantially parallel to one another and the blood vessel is positioned between the hinge portion and the lock portions when the blood vessel is ligated between the clamping surfaces in the closed position;
wherein in use the clip has a substantially smooth substantially spherical or substantially ovoid external 3-dimensional shape that is substantially free of:
i) external projections; and
ii) rough or sharp ends or rough or sharp edges so as to reduce the possibility of the clip eroding tissue structures surrounding the clip in vivo.

32. The method of claim 31 wherein in the clip the first direction is parallel to the pivot axis of the hinge portion.

33. The method of claim 31 wherein in the clip the first maximum dimension of the clip is at least about 0.6 times the second maximum dimension of the clip.

34. The method of claim 31 wherein in the clip the first maximum dimension of the clip is at least about 0.7 times the second maximum dimension of the clip.

35. The method of claim 31 wherein in the clip the first maximum dimension of the clip is at least about 0.8 times the second maximum dimension of the clip.

36. The method of claim 31 wherein in the clip the first maximum dimension of the clip is at least about 0.9 times the second maximum dimension of the clip.

37. The method of claim 31 wherein the blood vessel is a varicose vein.

38. The method of claim 31 wherein in the clip the first lock portion protrudes from the first clip portion and wherein the second lock portion is positioned to couple to the first clip portion.

39. The method of claim 31 wherein in the clip the first lock portion is provided with at least one barb and the second lock portion is arranged to receive the at least one barb so as to lock the clip portions together in use.

40. The method of claim 31 wherein in the clip the first lock portion is provided with at least one barb and the second lock portion is arranged to receive the at least one barb so as to lock the clip portions together, wherein the second lock portion is provided with at least one barb, and wherein at least one of the first and second lock portions is provided with a plurality of barbs to function like a locking ratchet when the clip portions are hinged to the closed clip condition.

41. The method of claim 40, wherein in the clip both of the first and second lock portions are provided with a plurality of barbs and wherein in use at least two barbs of the first lock portion are in contact with at least two barbs of the second lock portion to provide a plurality of barb-to-barb contacts.

42. The method of claim 41 wherein the plurality of barbs enable the clip portions to be locked together in a plurality of different closed clip conditions during use, each different closed clip condition representing a different spacing between the clip portions, such that the clip can ligate blood vessels within a range of different sizes.

43. The method of claim 31 wherein in the clip in use the clip has a substantially spherical external shape.

44. The method of claim 31 wherein in the clip both of the clip portions are substantially hemispherical in shape.

45. The method of claim 31 wherein in the clip in use the clip has a substantially oval external shape.

46. The method of claim 31 wherein in the clip both of the clip portions are substantially hemioval in shape.

47. The method of claim 31 wherein in the clip the stand-off gap between the clamping surfaces in a closed clip condition is at least 0.3 mm.

48. The method of claim 31 wherein in the clip the stand-off gap between the clamping surfaces in a closed clip condition is less than about 1 mm.

49. The method of claim 31 wherein in the clip the clip structure is non-metallic.

50. The method of claim 31 wherein in the clip the clip structure comprises polypropylene.

51. The method of claim 31 wherein in the clip the clip structure comprises nylon.

52. The method of claim 31 wherein in the clip the clip structure comprises polydiaxonone.

53. The method of claim 31 wherein in the clip the clip is provided in a sterile container.

54. The method of claim 31 wherein in the clip the stand-off gap between the clamping surfaces in a closed clip condition is less than about 0.5 mm.

55. The method of claim 31 wherein the clip further comprises surface undulation on the first clamping surface and the second clamping surface.

56. The method of claim 37 wherein the varicose vein comprises tributaries of the femoral vein.

57. The method of claim 31 wherein the blood vessel comprises saphenous vein tributaries.

58. The method of claim 31 wherein the blood vessel is a cystic artery.

* * * * *